United States Patent [19]

Hepp et al.

[11] Patent Number: 4,662,375
[45] Date of Patent: May 5, 1987

[54] ALLEVIATING PAIN DURING EXTRACOPORAL LITHOTRIPSY

[75] Inventors: Wolfgang Hepp, Immenstaad; Gerold Heine, Uhldingen; Othmar Wess, Immenstaad; Ernst Marlinghaus, Friedrichshafen, all of Fed. Rep. of Germany

[73] Assignee: Dornier System GmbH, Friedrichshafen, Fed. Rep. of Germany

[21] Appl. No.: 747,954

[22] Filed: Jun. 24, 1985

[51] Int. Cl.⁴ .............................................. A61B 17/22
[52] U.S. Cl. .................................. 128/328; 128/24 A
[58] Field of Search ...................... 128/804, 328, 24 A, 128/660

[56] References Cited

U.S. PATENT DOCUMENTS 4,539,989 9/1985 Forssmann et al. ................ 128/328

FOREIGN PATENT DOCUMENTS 131654 1/1985 European Pat. Off. ............ 128/328
2913251 10/1980 Fed. Rep. of Germany ...... 128/328

Primary Examiner—Clifford D. Crowder
Attorney, Agent, or Firm—Ralf H. Siegemund

[57] ABSTRACT

In extracorporal lithotripsy a shock wave that is focussed on a concrement is followed by a pain producing pressure wave. This wave is filtered by means of a membrane bulging inwardly into the focussing chamber, closing the same and having a thickness smaller than the predominant wave length of the shock wave.

13 Claims, 6 Drawing Figures

ALLEVIATING PAIN DURING EXTRACOPORAL LITHOTRIPSY

BACKGROUND OF THE INVENTION

The present invention relates to the aleviation or at least reduction and attenuation of pain that occurs during lithotripsy of patients who have not been anesthesized, the lithotripsy being carried out by means of acoustic shock waves and the inventive method and system is to be usable regardless of whether patient and shock wave source are submerged in a water bath or if the acoustic coupling is carried out through a limited water path without submersion of patient and equipment.

Shock wave lithotripsy will induce considerable pain if the patient is not anesthesized. As Schlieren investigations and pressure measurements have indicated the pain is attributable to a slow (i.e. long duration) pressure wave following immediately the shock wave proper; and due to the relative long lasting effect of this pressure wave (several milliseconds) the pain threshold is exceeded. The shock wave proper has a much shorter duration such as a half a microsecond. This shock wave comminutes a concrement in the body and because of its short duration it is hardly noticeable in terms of pain.

The production of shock waves under utilization of a submerged i.e. under water spark discharge or a corona discharge under water is, however, causally related to the formation of low frequency pressure components, because the expansion of the spark plasma to a relative large gaseous volume, within a water bath amounts to a rapid displacement of the surrounding water. This displacement results in low frequency pressure pulses of waxing and waning flows, and they can unimpededly escape through the opening in the ellipsoidal reflector facing the patient and reach the patient and act in effect like an impact blow.

German printed patent application No. 29 13 251 discloses a structure by means of which the shock wave generator is closed physically through a planar metallic membrane. However, it was found that the pressure wave causes unwanted bulging of the planar metal membrane, and upon recoiling of the membrane skin tissue can actually be clamped. This clamping of tissue can be avoided by utilization of a water bag being disposed between the membrane and the body of the patient, but that does not alleviate or attenuate the pain producing capability of the pressure wave itself.

German printed Pat. No. 21 51 247 (U.S. Pat. No. 3,942,531) discloses as an alternative to close the shock wave generator by means of an elastic membrane which abuts without formation of an air gap the body of the patient and, therefore, follows the contour of the body and the skin and forms certain natural bulges. This membrane avoids the clamping effect noticed above, but still passes unattenuated the shock wave as well as a subsequent pressure wave so that again pain is not reduced.

DESCRIPTION OF THE INVENTION

It is an object of the present invention to provide a new and improved method and equipment for contactless comminution of concrements by means of shock waves in a manner that alleviates pain particularly in unanesthetized patients.

It is a feature of the present invention to filter out and eliminate the long lasting pressure wave that follows the short duration shock wave to thereby attenuate and possibly eliminate the pain a nonanesthesized patient may experience otherwise.

It is a specific object of the present invention to provide a new method and equipment for avoiding and eliminating pain in nonanesthesized patients being subjected to extracorporal lithotripsy using a rotationally elliptical focusing chamber having shock wave source in one focal point while the concrement of the patient to be treated is located in the second focal point and under further utilization of a water bath for coupling the ellipsoidal focusing chamber to the patient.

In accordance with the preferred embodiment of the present invention it is suggested to close the focusing chamber by means of a shape-stable bulging spherical membrane having a wall thickness which is significantly smaller than the wave length of the shockwave and being oriented such that the bulge enters the ellipsoid. It is specifically suggested that the cross section of this membrane resembles an arch such that pressure loads will produce exclusively compressive stress. The center of curvature of the calotte is preferably situated in the second focal point of the ellipsoid which is supposed to coincide with the concrement. The edge of the calotte should be rigidly clamped to the edge of the ellipsoid by means of a ring fastened thereto by means of tension springs. The calotte should be made of a material having a high coefficient of elasticity such as steel, a Cu-Be alloy or a carbon fiber reinforced synthetic. For fully galvanic (direct current conduction) separation of the electrodes within the ellipsoid from that part of the equipment which is in immedaite contact with the patient, the calotte should be grounded; also stiffening and bending points should be provided for. The calotte should have on at least one side constructed as a facet structure and alternatively or in addition its center should be thinner than the remaining portion with continuous reduction of wall thickness towards the center; on the other hand the edge portions of the membrane may likewise be thinner than the membrane portion between center and edge. Elastically deformable elements should be provided in the vicinity of the arc discharge area with particular placement in recesses in the wall of the focusing chamber. The interior of the ellipsoid must receive water and it is therefore suggested to provide the water inlet as well as its discharge in the vicinity of the calotte so as to flush any gas bubbles off the membrane.

It was found that the invention does permit in fact attenuation, reduction and even elimination of pain resulting from the effects outlined above without affecting the comminution process by means of the shock wave and involving the destruction of a concrement. The invention in particular permits separation of the desired and effective shock wave from subsequent pressure waves such that only the shock wave in effect acts on the patient. This separation of the two basic components is made possible by the shaped stable shock wave permeable calotte as interposed between the point of shock wave generation and the patient generally. This kalotte in a highly unexpected fashion simply prevents the transfer or transmission of the long lasting pressure wave upon the patient.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings reference is first made to the diagram of FIG. 1. The figure shows in particular the pressure wave that is generated by an underwater spark within a focusing chamber of rotational-symmetrical, ellipsoidal configuration. The shock wave proper is produced in one of the focal points of this reflector and refocused in the second focal point. FIGS. 2 and 3 illustrate equipment for this purpose.

In FIG. 1 one can see that the time 0 is assumed to be the time of spark discharge, and immediately a shock wave is produced represented by a very steep rise towards a very high amplitude of the pressure. Moreover this shock wave occurs almost instantaneously and has therefore not only a very steep rise but also a steep trailing edge whereby the total duration is about half a microsecond. Generally speaking a pressure of 400 bars is typical for such a device. The pressure following that shock wave drops almost to zero but as a result of relaxation and other phenomena a pressure wave follows which has a relatively long duration in particular and is about 1000 fold longer than the initial shock wave; it lasts approximately 1.5 ms. A typical maximum amplitude for this pressure wave is between 100 mbar and 1 bar and is therefore significantly lower than the pressure peak of the shock wave. For this reason this shock wave does not participate in the comminution of the concrement. However as was outlined above it is this particular pressure wave, as was discovered, which causes significant pain in the patient if he or she is not anesthesized.

FIG. 2 illustrates the invention in conjunction with extracorporal lithotripsy devices for a procedure to be performed on a patient 2 whose body is supported in a water filled tub 6; the water bath being denoted by the reference numeral 4. It is assumed in particular that a kidney stone 10 is lodged in the kidney 8 of the patient 2. The principal instrument for the lithotripsy is a focusing chamber 12 having two focal points $F_1$ and $F_2$. The axis through these focal points constitutes an axis of symmetry of the ellipsoidal reflector.

Figure 1:
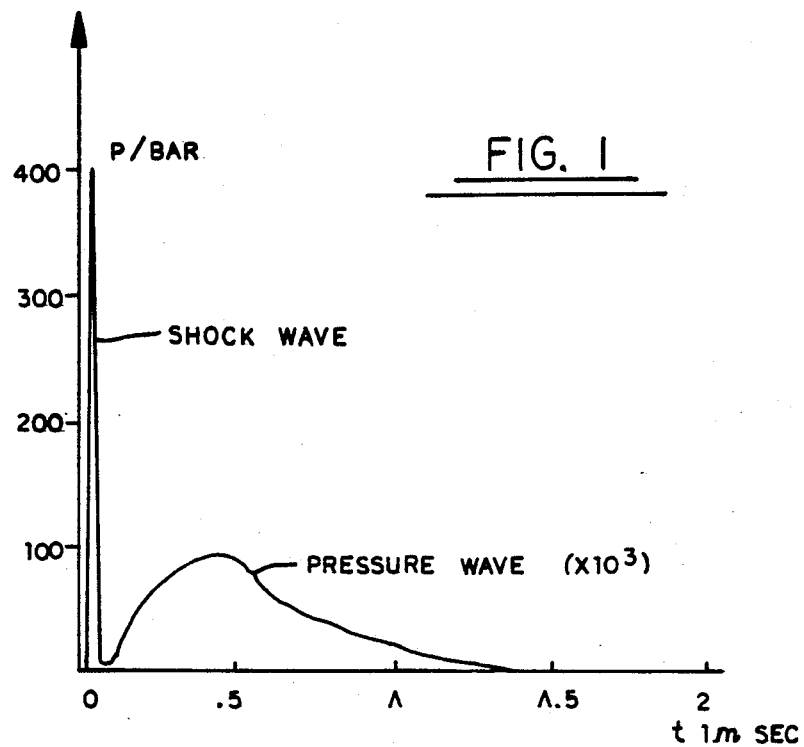
FIG. 1 illustrates a diagram in which pressure is plotted against time showing the shock wave as generated followed by a relatively long lasting pressure wave.

The ellipsoidal surface 22 of the focusing chamber is positioned such that the focal point $F_2$ coincides with or is situated somewhere within the kidney stone 10. A spark discharge is triggered and induced in the focal point $F_1$, and for this purpose two electrodes 16 and 18 are provided having discharge points being very close to each other and to the focal point $F_1$ so that a spark discharge between them coincides with the location of point $F_1$ as closely as possible. The electrodes 16 and 18 are maintained in an electrode holder 14 which traverses the wall of the focusing chamber.

The therapeutic shock wave as well as the subsequent parasitic pressure wave are produced whenever a spark discharge is between the points 16 and 18. The devices for the production of that spark are not shown in that figure, they are conventional. The shock produced in and very close to the focus F1 passes through the water that fills the interior of the focal chamber. The shock wave as reflected by the surface 22 is refocused and converges towards the focal point $F_2$ so as to obtain a high intensity shock wave within the kidney stone 10 causing spalling and other comminution.

The pressure wave following the shock wave is hardly or very little focused and just propagates through the water 20 within the ellipsoid 22. In the vicinity of the upper edge 24 of the ellipsoid a spherical calotte or a kalotte shaped membrane 26 is clamped and provided for inward bulging i.e. it bulges into the interior of the ellipsoid. As stated this calotte membrane 26 is clamped along the upper edge 24 of the ellipsoid. Owing to the bulging, the choice of material and of the wall thickness as well as on account of the rigid clamping along the edge 24, this calotte membrane 26 filters almost completely the entire pressure wave that follows the shock wavefront; while on the other hand the shock wavefront runs essentially parallel to the calotte as it converges towards F2 and is therefore not refracted. This aspect is enhanced by having the bulge of membrane chosen so that its radial center coincides with F2 towards which the shock wave fronts converge. Also it is not to be expected that gas bubbles will deposit on the calotte primarily because of the inward bulging.

The formation of gas bubbles can be prevented in addition by providing the water inlet 28 and the water outlet 30 for the interior of the ellipsoid quite close to the calotte i.e. in the immediate vicinity thereof. This way one produces in effect a tangential flow along the calotte membrane 26 and any air bubble that may form is immediately dislodged and will be discharged.

Figure 5:
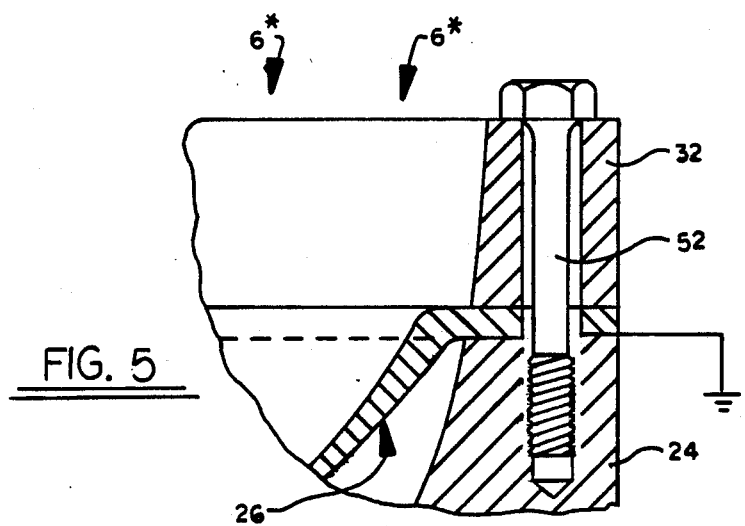
FIG. 5 is a cross section through a detail of FIG. 2.

The calotte membrane 26 is moreover forced by means of a pressure ring 32 onto the edge 24 of the focusing chamber and details are shown with reference to FIG. 5. The calotte here is particularly provided and fastened by means of a pressure ring 32 to the focusing chamber 12. In order to make sure that pressure waves are safely transmitted, received and conducted out of the system, the pressure ring 32 is fastened by means of tension screws 52. This type of screw has the property of elastically taking up tension loads. FIGS. 5 shows that part of a spherical calotte membrane in which the wall thickness continuously reduces from the edge to the center.

Figure 2:
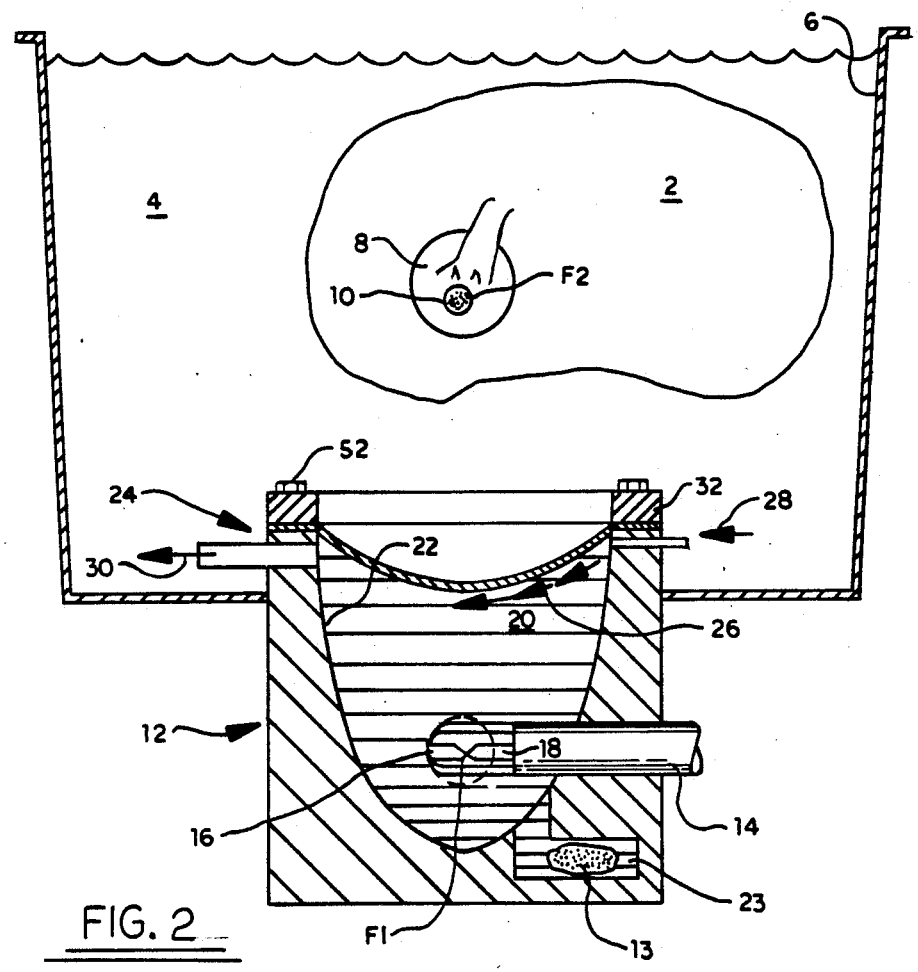
FIG. 2 illustrates in cross section a device for extracorporal lithotripsy using the inventive feature and under assumption that the patient is placed in a water containing tub.

A side duct 23 (FIGS. 2 and 3) contains an elastically deformable element 13 to compensate for the fact that water is basically an incompressable liquid. Element 13 absorbs a significant portion of the long lasting pressure wave. FIG. 5 shows also that the metallic membrane 26 is grounded for separating electrically the space above and below the membrane.

Figure 6:
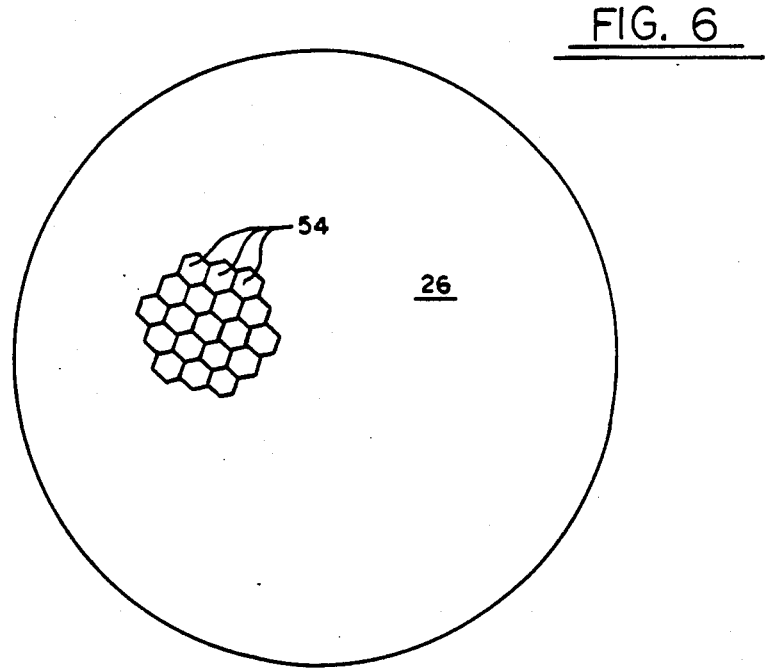
FIG. 6 is a view as indicated by arrows 6* in FIG. 5.
Figure 3:
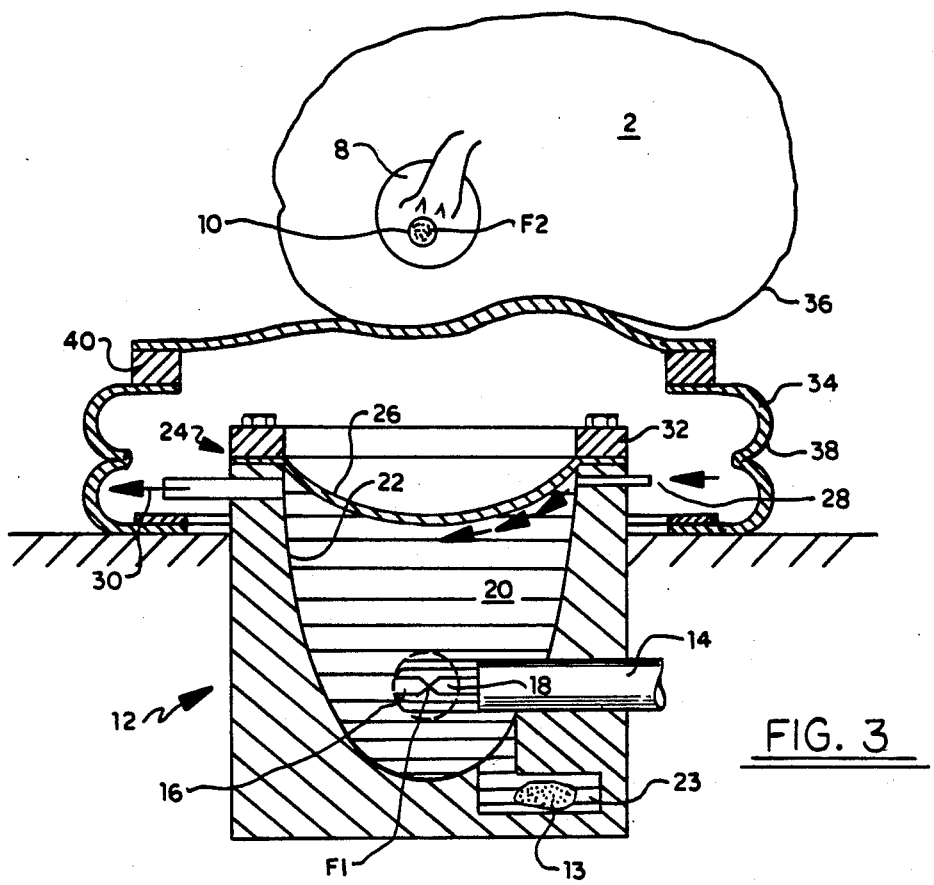
FIG. 3 is an analogous cross section showing similar equipment but without using tub in which the patient is placed.
Figure 4:
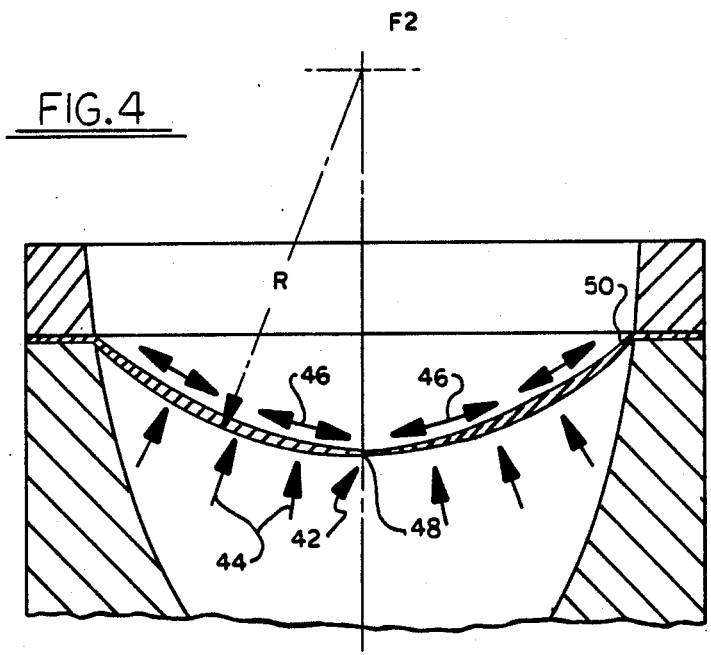
FIG. 4 is a cross section through a portion of the device as shown in FIGS. 2 and 3 and showing certain aspects in greater detail and on an enlarged scale.

FIG. 3 illustrates an example for extracorporal lithotripsy to be carried out without placing the patient 2 into a water filled tub. Instead, a water filled cushion 34 is provided in order to serve as a coupling medium between the focusing chamber 12 and the body 2. This cushion 34 is, on one hand, secured to the focusing chamber 12 while on the other hand it abuts and follows the contour of the body surface and skin 36 of the patient 2. The container-cushion 34 moreover is provided for further adaptation to the position of the patient with a folding bellows 38 and a ring 40. It should be noted that the calotte membrane 26 shown in FIGS. 2, 4 and/or 5 is the same as the calotte membrane shown in FIG. 3. Details of the inventive calotte of spherical configuration are shown in FIGS. 4-6. Basic aspects of FIG. 5 have already been described.

Turning particularly to FIG. 4 there is shown a spherical calotte 42 having a cross section which in effect resembles an arch. This kind of configuration has the property that pressure loads indicated by arrow 42 are effective as compressive stress as indicated by arrows 46. FIG. 4, moreover, shows specifically that the center of curvature of a circular calotte is preferably located in the second focal point $F_2$. There is, therefore, a definite geometric relationship between the reflective properties of the focusing chamber and the calotte shaped membrane.

FIG. 4 shows also that the wall thickness of the calotte membrane 42 in the center of 48 as well as in and near the edge zone 50 is smaller than elsewhere. The wall thickness of the spherical calotte membrane is chosen to be smaller everywhere than the predominant wavelength of the shock wave. It was found of advantage to make the calotte 42 of steel and in this case a maximum wall thickness of 0.3 mm was found quite suitable. As stated above FIG. 5 shows a different thickness profile as far as the calotte itself is concerned. Here the maximum wall thickness occurs on the edge, but still follows the rule expounded above relating shock wave duration to membrane thickness.

FIG. 6 shows a certain detail of the calotte membrane 26 (or 42) in top elevation. The particular membrane exhibits a facet structure provided in the material by means of punching or press working. The facets 54 can be hexagonal but any other geometric pattern is quite possible. Moreover, the calotte may have bending points in which bending occurs to the preferred degree in order to avoid that plastically deformed bulges occur anywhere.

It was mentioned that the spherical calotte can be made of steel. With or without facet structure other material of a high coefficient of elasticity is suitable. Among steel in particular alloyed and unalloyed steel can be used. Alternatively a Cu-Be alloy is quite suitable. In the alternative one can use as the membrane a carbon fibre reinforced synthetic such as (CFS).

An essential aspect of the calotte membrane is that even during a long lasting use its shape remains stable, and the geometrically predetermined calotte shape is in fact maintained. The bulging is particularly selected with the curvature occurring in relation to the focal point mentioned above. Wall thickness and clamping is critical for filtering of the pressure wave. By way of example:

| material. | coefficient of elasticity (mm) | wall thickness |
|---|---|---|
| steel 190 to 220 | $10^3$ N/mm$^2$ | 0.-0.5 |
| Cu—Be steel | 125 | 0.2-0.5 |
| CFS | 100 | 0.2-0.5. |

The invention is not limited to the embodiments described above but all changes and modifications thereof not constituting departures from the spirit and scope of the invention are intended to be included.

We claim:

1. In equipment for extracorporal lithotripsy of nonanesthesized patients and including a rotationally-symmetrical, ellipsoidal focusing chamber having two focal points there being a shock wave generating source in one of the focal points, the focusing chamber being positionable so that the other focal point coincides with a concrement in a patient, which concrement is to be comminuted by shock waves, there being a water coupling path between the focusing chamber on one hand and the patient on the other hand the improvement of avoiding and attenuating pain, comprising:
a spherically calotte shaped membrane made of a material with a high coefficient of elasticity and being clamped against and closing the focusing chamber and inwardly bulging towards the shock wave generating source, the wall thickness of the membrane being significantly shorter than the wavelength of a shock wave being produced.

2. The improvement as in claim 1 wherein the cross section of said membrane is an arch so that pressure loads will produce compression stress in the membrane.

3. The improvement as in claim 1 said membrane being configured so that its center of curvature coincides with said other focal point.

4. The improvement as in claim 1 wherein said calotte membrane is clamped to the edge of the focusing chamber under utilization of a ring and tension screws for fastening the ring to the focusing chamber.

5. The membrane as in claim 1 being made of steel.

6. The membrane as in claim 1 being made of a Cu-Be alloy.

7. The membrane as in claim 1 being made of a carbon fiber reinforced synthetic.

8. The improvement as in claim 1 including means for grounding for obtaining nonconduction and conductive separation between the interior of the focusing chamber containing the electrodes and any part that is in physical contact with a patient.

9. The membrane as in claim 1 having at least on one side a facet structure.

10. The membrane as in claim 1 having a center thinner than the remainder of the membrane, the wall thickness continuously decreasing towards the center.

11. The membrane as in claim 1 being thinner in the center as well as in the edges as compared with the remainder of the membrane.

12. The improvement as in claim 1 and including an elastically deformable element in the vicinity of said source, the element being situated in recesses in the wall of the focusing chamber.

13. The improvement as in claim 1 there being a water inlet and a water discharge for the focusing chamber being situated in the vicinity of said membrane.

* * * * *